(12) United States Patent
Kim et al.

(10) Patent No.: US 9,818,184 B2
(45) Date of Patent: Nov. 14, 2017

(54) METHOD FOR ACQUIRING AND PROCESSING MEDICAL IMAGES

(71) Applicant: THE ASAN FOUNDATION, Seoul (KR)

(72) Inventors: Jae Seung Kim, Seoul (KR); Jong Jin Lee, Seoul (KR); Jung Su Oh, Seoul (KR); Jae Kwang Ryu, Seoul (KR); Woo Young Jung, Seoul (KR)

(73) Assignee: THE ASAN FOUNDATION, Seoul (KR)

( * ) Notice: Subject to any disclaimer, the term of this patent is extended or adjusted under 35 U.S.C. 154(b) by 0 days.

(21) Appl. No.: 14/888,186

(22) PCT Filed: Mar. 28, 2014

(86) PCT No.: PCT/KR2014/002653
§ 371 (c)(1),
(2) Date: Oct. 30, 2015

(87) PCT Pub. No.: WO2014/178538
PCT Pub. Date: Nov. 6, 2014

(65) Prior Publication Data
US 2016/0110862 A1    Apr. 21, 2016

(30) Foreign Application Priority Data

Apr. 30, 2013  (KR) .................. 10-2013-0048128

(51) Int. Cl.
*G06K 9/00*     (2006.01)
*G06T 7/00*     (2017.01)
*A61B 6/03*     (2006.01)
*A61B 6/00*     (2006.01)
*G06T 7/38*     (2017.01)

(52) U.S. Cl.
CPC ............ *G06T 7/0012* (2013.01); *A61B 6/032* (2013.01); *A61B 6/037* (2013.01); *A61B 6/4417* (2013.01);
(Continued)

(58) Field of Classification Search
CPC ... G06T 7/0012; G06T 7/0081; G06T 7/0038; G06T 2207/10081; G06T 2207/10104;
(Continued)

(56) References Cited

U.S. PATENT DOCUMENTS

| 5,378,986 A | 1/1995 | Seo et al. ...................... 324/309 |
| 7,447,345 B2 | 11/2008 | Shanmugam et al. ........ 382/131 |

(Continued)

FOREIGN PATENT DOCUMENTS

| JP | 2006-320527 | 11/2006 | ............. A61B 5/055 |
| JP | 5148069 B2 | 2/2013 | ............. G01T 1/161 |
| KR | 10-2010-0060193 | 6/2010 | ............. A61B 5/055 |

OTHER PUBLICATIONS

International Search Report (ISR) dated Jun. 10, 2014 in PCT/KR2014/002653 with English translation.

*Primary Examiner* — John Strege
(74) *Attorney, Agent, or Firm* — Harness, Dickey & Pierce, P.L.C.

(57) ABSTRACT

Disclosed herein is a method for acquiring and processing a medical image, comprising obtaining the first to n-th sectional images of the first to n-th regions through non-sequential sectional-image acquisition starting from one of the first to n-th regions and sequentially arranging the obtained first to n-th sectional images.

13 Claims, 8 Drawing Sheets

(52) U.S. Cl.
CPC .............. *A61B 6/54* (2013.01); *G06T 7/38* (2017.01); *G06T 2207/10081* (2013.01); *G06T 2207/10104* (2013.01); *G06T 2207/20221* (2013.01); *G06T 2210/41* (2013.01)

(58) Field of Classification Search
CPC ....... G06T 2207/20221; G06T 2207/41; A61B 6/032; A61B 6/4417; A61B 6/54; A61B 6/037
USPC ......................................................... 382/128
See application file for complete search history.

(56) References Cited

U.S. PATENT DOCUMENTS

| | | | |
|---|---|---|---|
| 8,643,641 B2* | 2/2014 | Passmore | G06T 7/2053 345/419 |
| 2008/0056437 A1* | 3/2008 | Pack | G01T 1/2985 378/10 |
| 2011/0222020 A1* | 9/2011 | Izatt | A61B 3/102 351/205 |
| 2013/0114879 A1* | 5/2013 | Scheid | G06T 7/001 382/145 |
| 2013/0195241 A1* | 8/2013 | Lee | G01N 23/046 378/41 |
| 2013/0265046 A1* | 10/2013 | Koch | G01R 33/56536 324/309 |
| 2016/0003928 A1* | 1/2016 | Chen | G01R 33/5611 324/309 |

* cited by examiner

METHOD FOR ACQUIRING AND PROCESSING MEDICAL IMAGES

CROSS-REFERENCE TO RELATED APPLICATIONS

This application is a national phase application of PCT Application No. PCT/KR2014/002653, filed on 28Mar. 2014, which claims benefit of Korean Patent Application KR 10-2013-0048128, filed on30 Apr. 2013. The entire disclosure of the application identified in this paragraph is incorporated herein by reference.

FIELD

The present disclosure generally relates to a method for acquiring and processing a medical image and, more particularly, to a method for acquiring and processing a medical image, which is capable of reducing an error attributable to a movement of a patient.

BACKGROUND

This section provides background information related to the present disclosure which is not necessarily a prior art.

FIG. 1 is a schematic view showing an example of a system and method for generating Positron Emission Tomography (PET)-Computed Tomography (CT) images disclosed in U.S. Pat. No. 7,447,345. FIG. 1 shows a PET-CT scanner 100. The PET-CT scanner 100 includes a CT system 200 and a PET system 300. The CT system 200 and the PET system 300 are mounted on a housing 120. Furthermore, the PET-CT scanner 100 includes a patient table 113, a bed 114, a processing unit 150, and a control station 115. The bed 114 is movable to the housing 120 by a manipulation of the control station 115. In general, the control station 115 includes a monitor and a keyboard. The processing unit 150 processes medical images obtained by the CT system 200 and the PET system 300 in response to a manipulation of the control station 115.

A Positron Emission Computed Tomography (PET) test is an advanced nuclear medicine image test method for dosing positron emission radioactive isotopes, obtaining radiation emitted outside the body, and obtaining useful diagnostic information related to a metabolic change of the body. Recently, this technology takes a step forward from obtaining only simple PET images and gradually evolves into a hybrid scanner into which even Computed Tomography (CT) equipment or Magnetic Resonance Image (MRI) equipment has been fused. In the current PET test, a PET/CT scanner in which a PET system and a CT system are coupled to the same body is used, and anatomical information from a CT image is obtained, so that the precise position and depth information of a lesion checked in a PET image can be provided.

Such a fusion or alignment (or registration) of images is possible when a sequentially obtained CT image and PET image are completely matched up with each other basically on the same plane, that is, when the two images are accurately matched (i.e., accurate registration). If a mismatch (i.e., mismatch registration) occurs between the two images due to a problem in a test, there is a limit in providing position information, that is, the original object of the fusion or alignment.

In particular, in a PET image, partial images at the positions of the bed 114 corresponding to a length of about 20 cm or less may be obtained due to a limit of an axial field of view (aFOV) inside and outside the length and a total body image may be configured by combining the partial images. In general, it is a precondition that a movement of a patient be minimized during a test in obtaining a medical image obtained by combining images at several bed positions. For example, such a problem may not be easily solved because the time taken to obtain a PET image, for example, is currently about 15 minutes. Furthermore, when a test is performed from the head to the feet, problems, such as the generation of an image artifact and a loss of a lesion near the pelvis area, are generated due to radioactivity of remaining urine filled in a bladder. For this reason, a test is performed from the feet to the head. If a test is performed from the feet to the head, however, an image mismatch near the head and a neck part attributable to a movement of the head during the test is frequently monitored while the head is photographed. FIGS. 2 and 3 are photographs showing an example in which a mismatch has occurred in a fusion image of a PET image and a CT image due to a movement of the head of a patient who experiences a total body PET test during the test. FIG. 2 is a transverse photograph in which a mismatch has occurred in the head, and FIG. 3 is a transverse photograph in which a mismatch has occurred a nose portion. FIG. 4 is a photograph showing a mismatch between a PET image and a CT image attributable to a movement of an arm during a test and an image artifact corresponding to the mismatch.

SUMMARY OF THE INVENTION

The problems to be solved by the present disclosure will be described in the latter part of the detailed description.

This section provides a general summary of the disclosure and is not a comprehensive disclosure of its full scope or all of its features.

According to one aspect of the present disclosure, in a method for obtaining and processing a medical image, the medical image is obtained from the first point of a target whose medical image is to be generated to a second point opposite the first point, and the medical image is the sum of images obtained in regions (wherein a region including the first point is a first region, a region including the second point is an n-th region, an image corresponding to the first region is defined to be a first sectional image, and an image corresponding to the n-th region is defined to be an n-th sectional image) obtained by dividing a region between the first point and the second point n times (wherein n>2, n is a positive integer greater than 2). Defining that sequentially obtaining the first sectional image to the n-th sectional image from the first region to the n-th region or sequentially obtaining the n-th sectional image to the first sectional image from the n-th region to the first region is sequential sectional-image acquisition, the method includes obtaining the first to n-th sectional images of the first to n-th regions through non-sequential sectional-image acquisition starting from one of the first to n-th regions and sequentially arranging the obtained first to n-th sectional images.

The advantageous effects of the present disclosure will be described in the latter part of the detailed description.

DETAILED DESCRIPTION

The present disclosure will now be described in detail with reference to the accompanying drawings.

Figure 5:
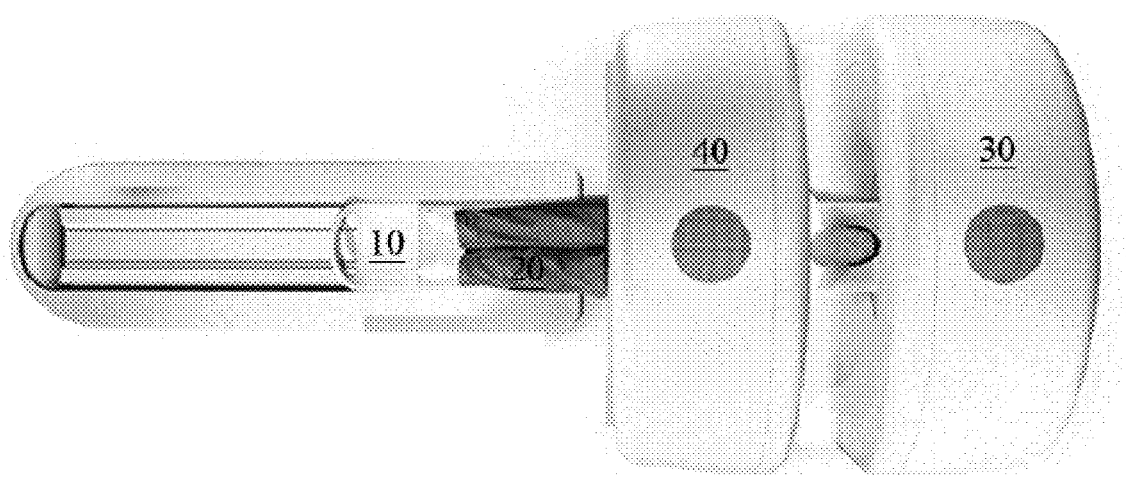
FIG. 5 is a schematic view showing an example of an apparatus for obtaining (or acquiring) and generating a medical image which may be used in the present disclosure.

FIG. 5 is a schematic view showing an example of an apparatus for obtaining (or acquiring) and generating a medical image which may be used in the present disclosure. FIG. 5 shows a bed 10, a target 20 from which a medical image is to be generated, and a medical image apparatus 30. A medical image apparatus 40 may be further included. The target 20 is commonly a person, but may be an animal. The bed 10 moves continuously or intermittently with respect to the medical image apparatus 30, so the target 20 moves to a position where a medical image is able to be obtained or acquired. Accordingly, the medical image apparatus 30 may generate a medical image by obtaining images from the target 20 continuously or intermittently. A system may be configured so that the medical image apparatus 30 is moved. For example, the medical image apparatus 30 may consist of a PET apparatus, and the medical image apparatus 40 may consist of a CT apparatus, but the present disclosure is not limited thereto. In this case, first, a CT image is obtained by passing the target 20 through the medical image apparatus 40 using the bed 10. In general, the time taken to obtain the CT image is within about 1 minute. Next, a PET image is obtained by sequentially moving the target 20 from the head to the feet with respect to the medical image apparatus 30 using the bed 10. The time taken to obtain the PET image is longer than about 10 minutes. At this time, the head of the patient may be moved. If the obtained PET image and CT image are registered (or aligned) or fused, a mismatch occurs between the PET image and the CT image.

Figure 6:
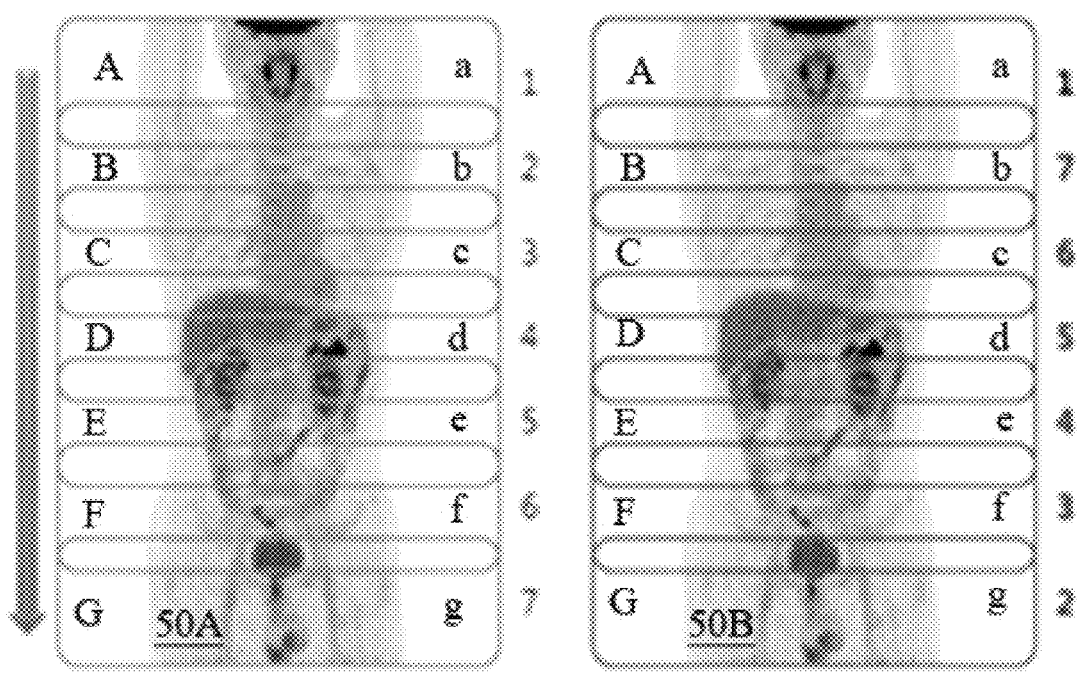
FIG. 6 is an image view showing an example of a medical image processing method according to an embodiment of the present disclosure.

FIG. 6 is an image view showing an example of a medical image processing method according to an embodiment of the present disclosure. For a comparison, a conventional medical image processing method and an example of the medical image processing method according to an embodiment of the present disclosure are shown on the left and right sides in FIG. 6. In the conventional medical image processing method, first to seventh sectional images "a" to "g" are sequentially obtained from the head to the feet with respect to seven regions A to G or bed positions. A medical image 50A is generated by arranging the sectional images. In this case, the first region A placed at the first place may be called a first point, and the seventh region G placed at the last place may be called a second point. In this case, the first to seventh sectional images "a" to "g" are sequentially obtained from the first point to the second point (this is defined as "sequential sectional-image acquisition"). In the case of the example of the present disclosure, likewise, a first sectional image "a" is obtained with respect to the first region A, that is, the first point, but thereafter seventh to second sectional images "g" to "b" are sequentially obtained from the second point (i.e., "non-sequential sectional-image acquisition"). The first to seventh sectional images "a" to "g" are sequentially arranged and a medical image 50B is then generated through the processing unit 150, such as that shown in FIG. 1. If the apparatus for obtaining and generating a medical image shown in FIG. 5 is used, the medical image 50B may be an image having a single modality, but may be an image into which an image of a different modality generated by the medical image apparatus 40 has been fused. A conventional medical image registration scheme is used in such a fusion and has been well known to those skilled in the art. If a medical image is obtained through the method proposed by FIG. 6, problems attributable to a movement in the process of obtaining the medial image can be solved because a sectional image of a portion which may be moved during the process is first obtained. Division images of the second region B (and the third region C) may be early obtained so that the head and/or the neck which may be moved are included. Furthermore, in the case of a PET image, problems attributable to a movement of the head are removed and a sectional image near the pelvis area is obtained subsequently thereafter, so that a pelvis image in which artifacts attributable to the accumulation of activities within a bladder are reduced, can be obtained.

Figure 7:
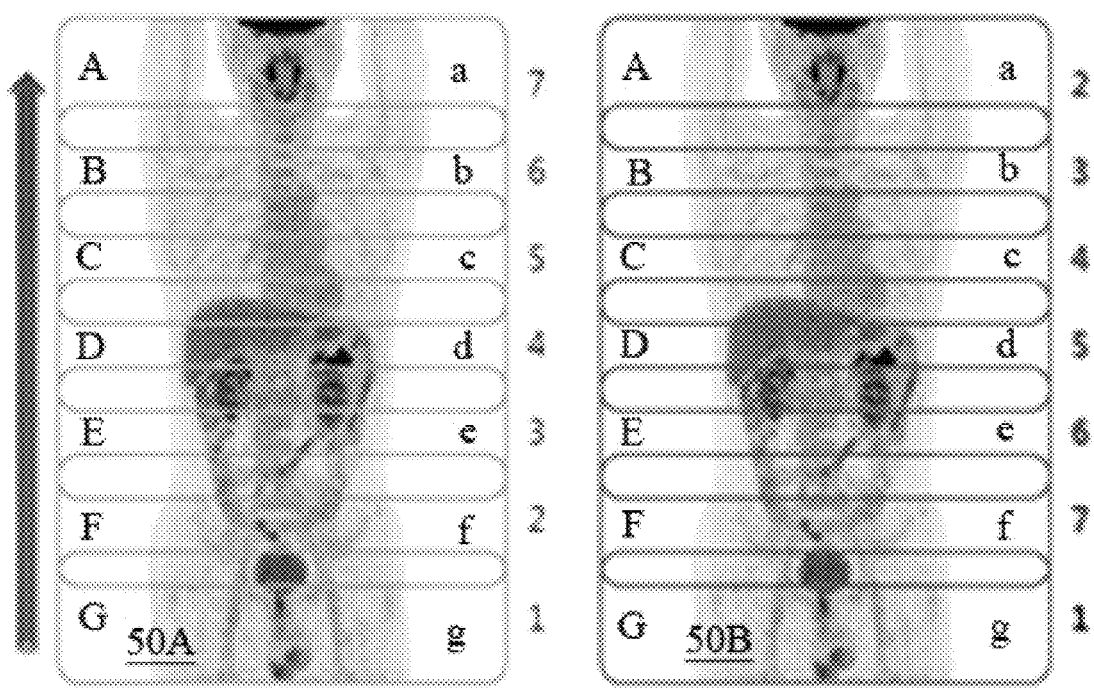
FIG. 7 is an image view showing another example of a medical image processing method according to an embodiment of the present disclosure.

FIG. 7 is an image view showing another example of a medical image processing method according to an embodiment of the present disclosure. For a comparison, a conventional medical image processing method and an example of the medical image processing method according to an embodiment of the present disclosure are shown on the left and right sides in FIG. 7. In the conventional medical image processing method, seventh to first sectional images "g" to "a" are sequentially obtained through sequential sectional-image acquisition from the head to the feet with respect to seven regions A to G or bed positions. A medical image 50A is generated by arranging the sectional images. In the case of the example of the present disclosure, likewise, a seventh sectional image "g" is obtained with respect to the seventh region G, that is, the second point, but thereafter first to sixth sectional images "a" to "f" are sequentially obtained from the first (i.e., "non-sequential sectional-image acquisition"). The first to seventh sectional images "a" to "g" are sequentially arranged and a medical image 50B is then generated through the processing unit 150, such as that shown in FIG. 1. In the case of a PET image, if a primary interest is an image test near the pelvis, the pelvis region is first photographed at 1~2 bed positions, a movement is performed toward the head, and the remaining regions are photographed. Accordingly, images having remaining activities not accumulated within a bladder and images of the head and/or the neck having a movement relatively reduced can be obtained or acquired.

Those skilled in the art will easily understand that a primary interest region or a region having a movement must be placed only at the first point or the second point, that is, both ends of a medical image. If a primary interest region or a region having a movement is placed between the first point and the second point, an image on the region or images on the region and nearby region(s) may be first obtained. Next, images of the remaining regions may be obtained from any one of the first point and the second point, if necessary.

Furthermore, those skilled in the art will easily understand that a plurality of primary interest regions and/or a plurality of regions having a movement may be present. In this case, medical images may be obtained according to priority. Furthermore, if a plurality of medical images needs to be registered, an image of a region that can be easily registered, that is, an image of a region including indices that can be easily recognized anatomically, may be first obtained. By taking into consideration such points, in the method for obtaining and processing a medical image according to an embodiment of the present disclosure, if sectional images of three or more regions are to be obtained and a medical image is to be generated by combining the three or more images, sequential sectional-image acquisition is not performed using a sectional image as the first point or the second point, but the three or more sectional images are obtained through non-sequential sectional-image acquisition starting from any one of the first point to the second point. Next, a medical image may be obtained by sequentially arranging the obtained images from the first point to the second point or from the second point to the first point.

Figure 1:
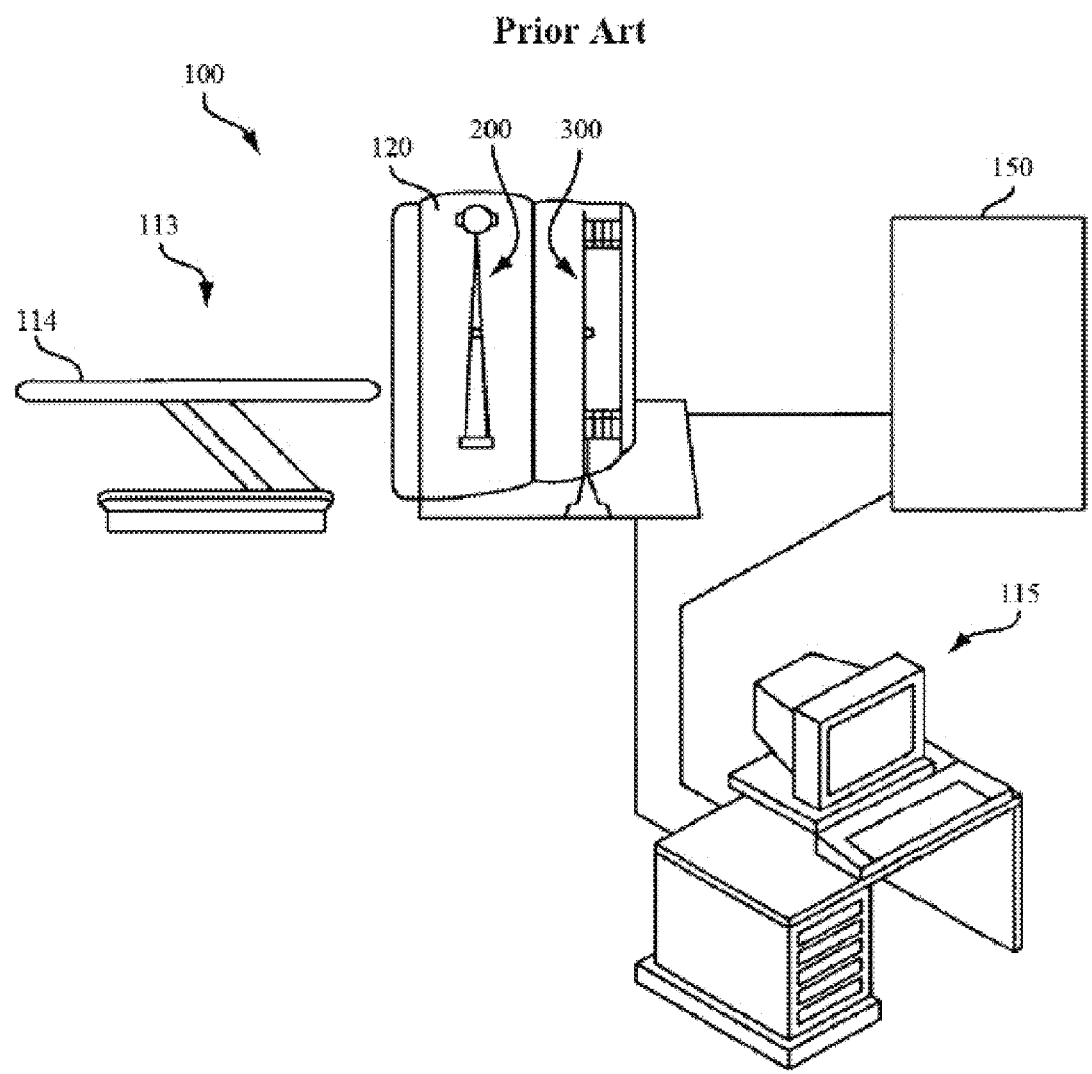
FIG. 1 is a schematic showing an example of a system and method for generating PET-CT images disclosed in U.S. Pat. No. 7,447,345.
Figure 2:
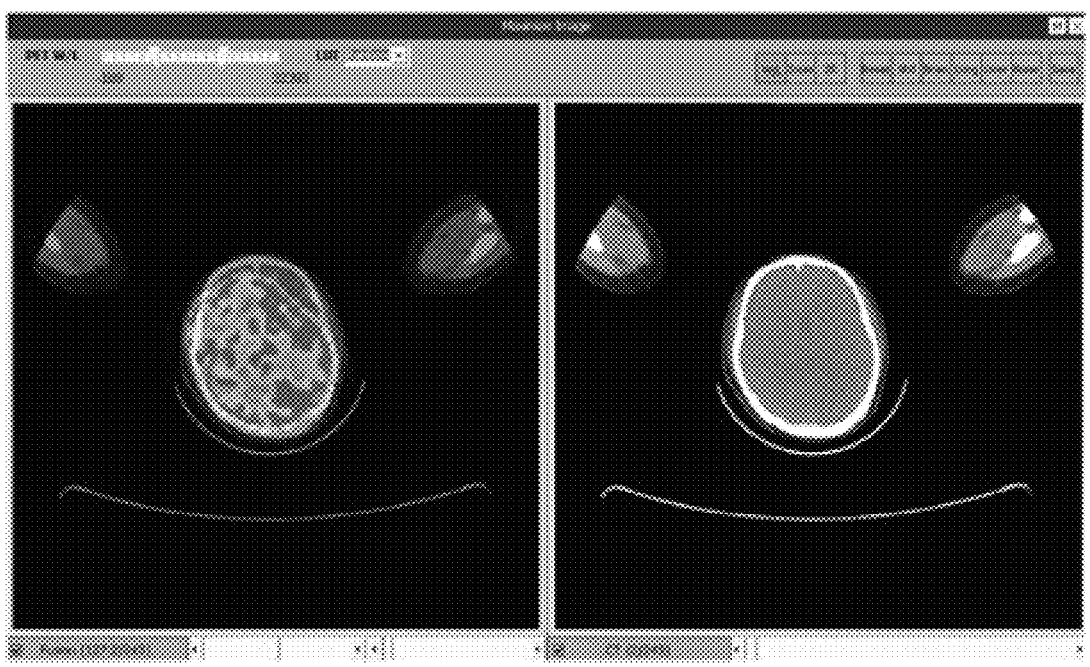
FIGS. 2 and 3 are photographs showing an example in which a mismatch has occurred in a fusion image of a PET image and a CT image due to a movement of the head of a patient who experiences a total body PET test during the test.
Figure 3:
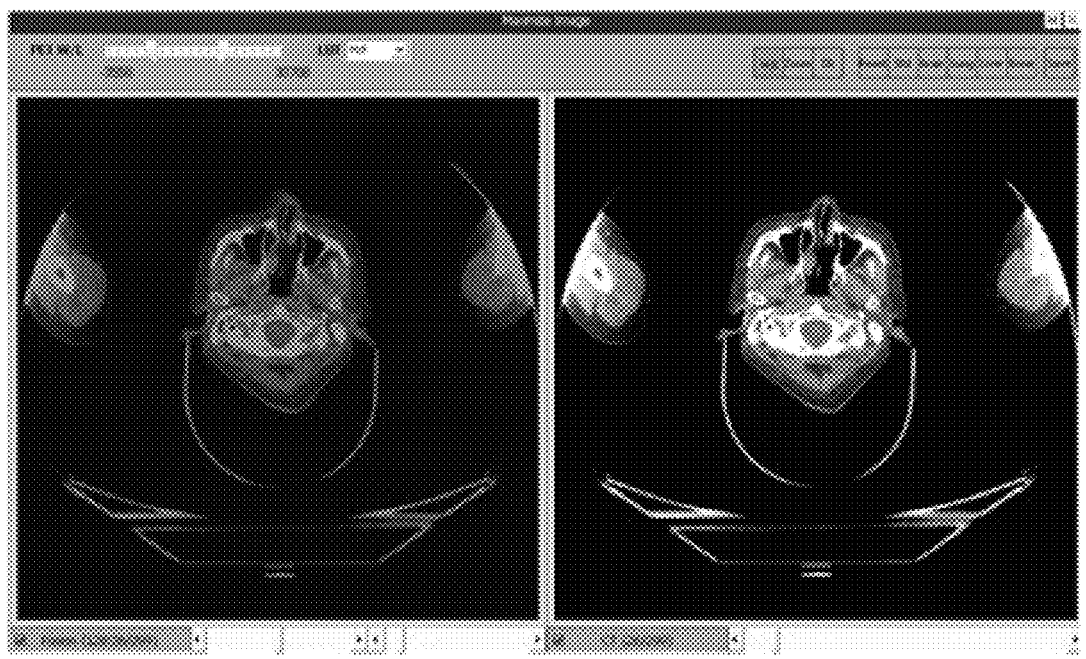
Figure 4:
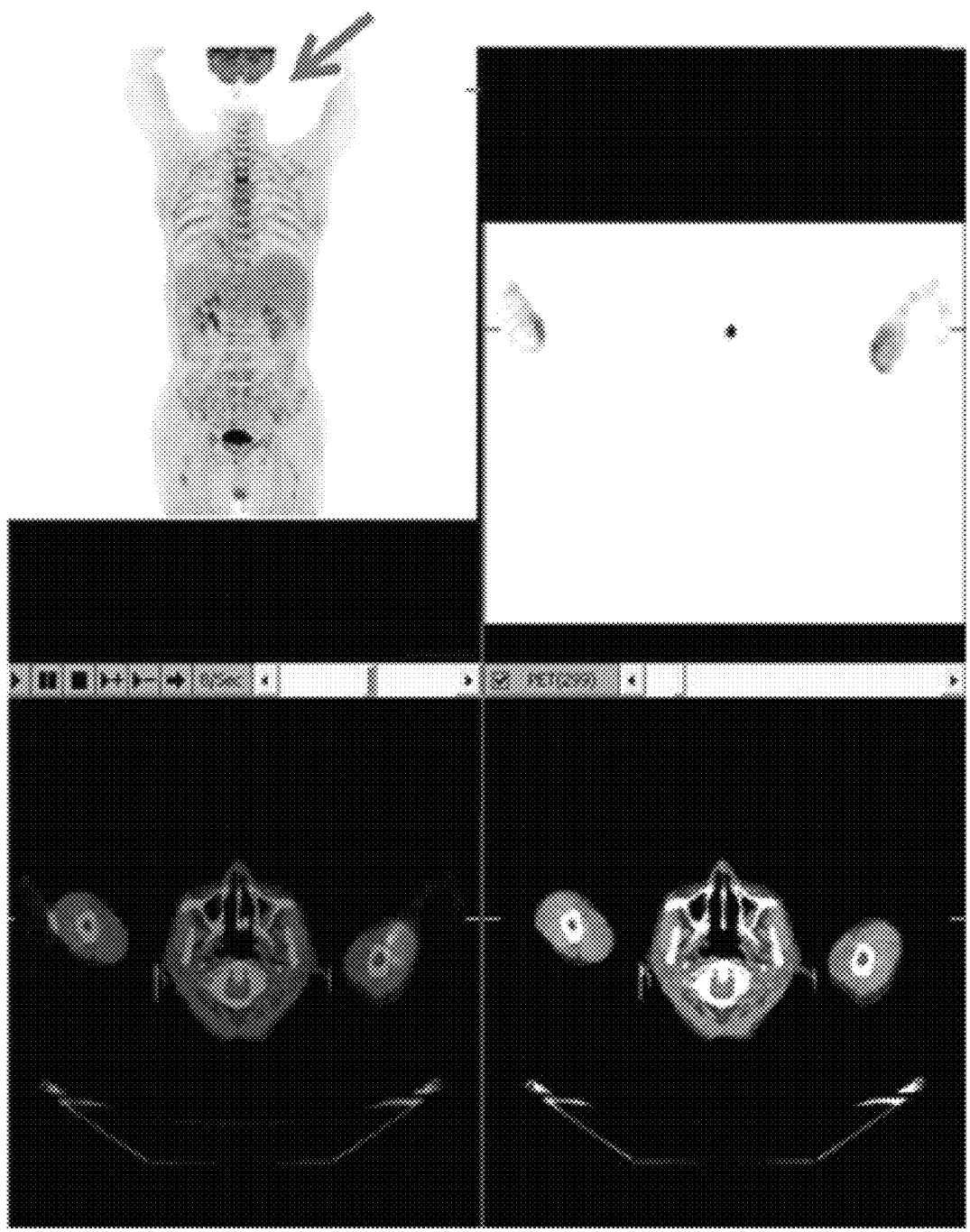
FIG. 4 is a photograph showing a mismatch between a PET image and a CT image attributable to a movement of an arm during a test and an image artifact corresponding to the mismatch.

The method for obtaining and processing a medical image according to an embodiment of the present disclosure may be particularly suitable for an apparatus for obtaining and generating a medical image in which two medical image apparatuses, such as those shown in FIGS. 1 and 4, have been combined, but the present disclosure is not limited to such an application. Furthermore, the method for obtaining and processing a medical image according to an embodiment of the present disclosure may be particularly suitable for an image including information about functional elements within the human body, such as a PET image, but the present disclosure is not limited thereto. If a medical image including information about functional elements within the human body and an image including anatomical information about the human body are combined and used, a corresponding problem (e.g., artifacts in a bladder) can be solved, and information about functional elements within the human body and information about anatomical elements can be accurately used at the same time.

Figure 8:
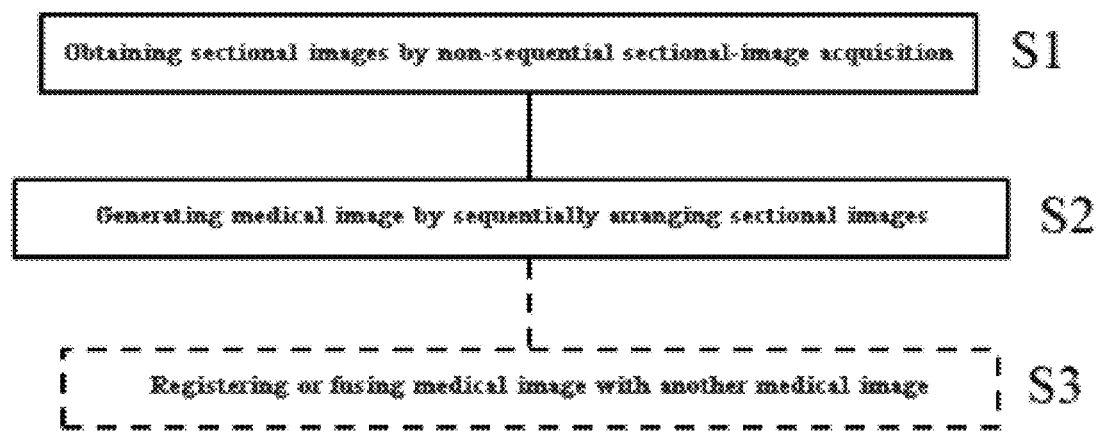
FIG. 8 is a flowchart illustrating an example of a method for obtaining and processing a medical image according to an embodiment of the present disclosure.

FIG. 8 is a flowchart illustrating an example of a method for obtaining and processing a medical image according to an embodiment of the present disclosure. The method for obtaining and processing a medical image according to an embodiment of the present disclosure includes obtaining sectional images through non-sequential sectional-image acquisition at step S1 and generating a medical image by sequentially arranging the sectional images at step S2 and may further include registering or fusing the medical image with another medical image, if necessary, at step S3. If the method according to an embodiment of the present disclosure is applied to the apparatus shown in FIGS. 1 and 4, a separate change of hardware is not required, and the method according to an embodiment of the present disclosure can be implemented by simply changing sequence of a movement of the bed 114 and sequentially arranging sectional images obtained by the medical image apparatus 300 in a process of assembling the sectional images.

Various embodiments of the present disclosure will now be described.

(1) A method for acquiring and processing a medical image, wherein the medical image is obtained from a first point of a target whose medical image is to be generated to a second point opposite the first point and the medical image is a sum of images obtained in regions (wherein a region comprising the first point is a first region, a region comprising the second point is an n-th region, an image corresponding to the first region is defined to be a first sectional image, and an image corresponding to the n-th region is defined to be an n-th sectional image) obtained by dividing a region between the first point and the second point n times (wherein n>2, n is a positive integer greater than 2), wherein defining that sequentially obtaining the first sectional image to the n-th sectional image from the first region to the n-th region or sequentially obtaining the n-th sectional image to the first sectional image from the n-th region to the first region is sequential sectional-image acquisition, the method comprising: obtaining the first to n-th sectional images of the first to n-th regions through non-sequential sectional-image acquisition starting from one of the first to n-th regions; and sequentially arranging the obtained first to n-th sectional images. Herein, the first point and the second points mean either end from which the medical image is generated. There is no need that the first point should be a head region and the second point should be a leg portion.

(2) A method for acquiring and processing a medical image, wherein the first to n-th sectional images are obtained by a first medical image apparatus which is relatively movable along the first to n-th division regions with respect to the target whose medical image is to be generated.

(3) A method for acquiring and processing a medical image, further comprising registering the medical image with a second medical image of the target whose medical image is to be generated. Herein, usually the second medical image has a modality different from the first modality of the first medical image but the second medical image may have the first modality which is obtained at a different time. For example, In case the first medical image is a PET image, the second medical image may be a CT image, a MRI image and so on. Also, the present disclosure can be applicable to two PET images obtained at different times. Besides, three images may be registered. For example, a PET image, a MRI image and a CT image can be registered. Preferably, an image representing any functional information on the target and an image representing any anatomical information on the target is used for registration.

(4) A method for acquiring and processing a medical image, further comprising registering the medical image with a second medical image of the target whose medical image is to be generated, wherein the second medical image is obtained by a second medical image apparatus provided in a relative moving direction of the first medical image apparatus.

(5) A method for acquiring and processing a medical image, wherein the medical image is a PET image.

(6) A method for acquiring and processing a medical image, wherein in obtaining the first to n-th sectional images, the first to m-th sectional images (wherein m is an integer and $1 \leq m < n$) are obtained starting from the first point and the n-th to (m+1)-th sectional images are obtained starting from the second point.

(7) A method for acquiring and processing a medical image, wherein the first to m-th sectional images comprise information about a head and neck of the target whose medical image is to be generated. By means of this, even though the head and the neck is moved after imaging, the problem occurring due to the movement of the head and the neck can be reduced.

(8) A method for acquiring and processing a medical image, wherein the first to m-th sectional images comprise information about a pelvis of the target whose medical image is to be generated.

(9) A method for acquiring and processing a medical image, wherein in obtaining the first to n-th sectional images, after p-th to q-th sectional images (wherein p is an integer, 1<p<n, q is an integer, and p≤q<n) are obtained, remaining sectional images are obtained.

(10) A method for acquiring and processing a medical image, further comprising registering the medical image with a second medical image of the target whose medical image is to be generated, wherein the first to n-th sectional images are obtained by a first medical image apparatus which is relatively movable along the first to n-th division regions with respect to the target whose medical image is to be generated, and the second medical image is obtained by a second medical image apparatus provided in a relative moving direction of the first medical image apparatus.

(11) Even though the present disclosure is explained mainly using a PET image and a CT image in the above, the present disclosure is extended to a MR image, a SPECT (Single Photon Emission Computed Tomography) image and an optical Tomography image and so on.

In accordance with the method for obtaining and processing a medical image according to an embodiment of the present disclosure, problems in generating a medical image through sequential sectional-image acquisition can be solved.

What is claimed is:

1. A method for acquiring and processing a medical image for a human body or an animal body, wherein the medical image is obtained from a first point of a target whose medical image is to be generated to a second point opposite the first point and the medical image is a sum of images obtained in regions (wherein a region comprising the first point is a first region, a region comprising the second point is an n-th region, an image corresponding to the first region is defined to be a first sectional image, and an image corresponding to the n-th region is defined to be an n-th sectional image) obtained by dividing a region between the first point and the second point n times (wherein n>2, n is a positive integer greater than 2), Wherein defining that sequentially obtaining the first sectional image to the n-th sectional image from the first region to the n-th region or sequentially obtaining the n-th sectional image to the first sectional image from the n-th region to the first region is sequential sectional-image acquisition, the method comprising:

obtaining the first to n-th sectional images of the first to n-th regions through non-sequential sectional-image acquisition starting from one of the first to n-th regions;

sequentially arranging the obtained first to n-th sectional images; and registering the medical image with a second medical image of the target whose medical image is to be generated, wherein more time is needed in obtaining the medical image than in obtaining the second medical image;

wherein in obtaining the first to n-th sectional images through non- sequential sectional-image acquisition, after p-th to q-th sectional images including a primary interest region or a region having a movement (wherein p is an integer, 1≤p<n, q is an integer, and p≤q<n) are obtained, remaining sectional images are obtained.

2. The method of claim 1, wherein the first to n-th sectional images are obtained by a first medical image apparatus which is relatively movable along the first to n-th division regions with respect to the target whose medical image is to be generated.

3. The method of claim 2, further comprising registering the medical image with a second medical image of the target whose medical image is to be generated, wherein the second medical image is obtained by a second medical image apparatus provided in a relative moving direction of the first medical image apparatus.

4. The method of claim 1, wherein the medical image is a PET image.

5. The method of claim 1, wherein in obtaining the first to n-th sectional images, the first to m-th sectional images (wherein m is an integer and 1≤m<n) are obtained starting from the first point and the n-th to (m+1)-th sectional images are obtained starting from the second point.

6. The method of claim 5, wherein the first to m-th sectional images comprise information about a head and neck of the target whose medical image is to be generated.

7. The method of claim 5, wherein the first to m-th sectional images comprise information about a pelvis of the target whose medical image is to be generated.

8. The method of claim 1, further comprising registering the medical image with a second medical image of the target whose medical image is to be generated, wherein the first to n-th sectional images are obtained by a first medical image apparatus which is relatively movable along the first to n-th division regions with respect to the target whose medical image is to be generated, and the second medical image is obtained by a second medical image apparatus provided in a relative moving direction of the first medical image apparatus.

9. The method of claim 8, wherein the medical image is a PET image.

10. The method of claim 9, wherein the second medical image is a CT image.

11. The method of claim 10, wherein in obtaining the first to n-th sectional images, the first to m-th sectional images (m is an integer and 1≤m<n) starting from the first point, and the n-th to (m+1)-th sectional images are obtained starting from the second point.

12. The method of claim 11, wherein the first to m-th sectional images comprise information about a head and neck of the target whose medical image is to be generated.

13. The method of claim 11, wherein the first to m-th sectional images comprise information about a pelvis of the target whose medical image is to be generated.

* * * * *